(12) United States Patent
Dugrot (10) Patent No.: US 8,460,253 B2
(45) Date of Patent: Jun. 11, 2013

(54) MAGNETICALLY SEALED INTRAVENOUS ACCESS VALVE

(76) Inventor: Manuel Dugrot, N. Miami, FL (US)

(*) Notice: Subject to any disclaimer, the term of this patent is extended or adjusted under 35 U.S.C. 154(b) by 369 days.

(21) Appl. No.: 12/983,755

(22) Filed: Jan. 3, 2011

(65) Prior Publication Data

US 2012/0172819 A1    Jul. 5, 2012

(51) Int. Cl.
*A61M 5/00* (2006.01)
(52) U.S. Cl.
USPC .......................................................... 604/256
(58) Field of Classification Search
USPC ................................ 604/256, 246, 93.01, 248
See application file for complete search history.

(56) References Cited

U.S. PATENT DOCUMENTS

| | | | |
|---|---|---|---|
| 3,105,511 A * | 10/1963 | Murphy, Jr. | 137/399 |
| 3,777,737 A * | 12/1973 | Bucalo | 128/843 |
| 4,865,588 A * | 9/1989 | Flinchbaugh | 604/129 |
| 4,994,020 A * | 2/1991 | Polyak | 600/31 |
| 5,114,412 A * | 5/1992 | Flinchbaugh | 604/247 |
| 5,637,083 A * | 6/1997 | Bertrand et al. | 604/9 |
| 6,673,051 B2 * | 1/2004 | Flinchbaugh | 604/247 |
| 6,695,004 B1 * | 2/2004 | Raybuck | 137/433 |
| 6,736,797 B1 | 5/2004 | Larsen et al. | |
| 6,926,694 B2 | 8/2005 | Marano-Ford et al. | |
| 7,025,741 B2 * | 4/2006 | Cull | 604/9 |
| 7,128,730 B2 | 10/2006 | Marano-Ford et al. | |
| 7,282,023 B2 * | 10/2007 | Frering | 600/31 |
| 2006/0064159 A1 | 3/2006 | Porter et al. | |
| 2008/0147012 A1 | 6/2008 | Rome | |
| 2009/0036910 A1 * | 2/2009 | Kim et al. | 606/157 |
| 2009/0275893 A1 | 11/2009 | DiBiasio et al. | |

FOREIGN PATENT DOCUMENTS

EP        0 239 244        9/1987

* cited by examiner

Primary Examiner — Kevin C Sirmons
Assistant Examiner — Michael J Anderson
(74) Attorney, Agent, or Firm — Richard C. Litman (57) ABSTRACT

The magnetically sealed intravenous access valve is an implantable port and valve for vascular access. The magnetically sealed intravenous access valve includes a housing and a pair of hollow tubes provided for interconnection and communication with the patient's blood vessel. Each tube is partially slidably received within a lower portion of the housing. A hollow key is used to selectively open and close the valve and also to inject medication into the patient's blood vessel. The hollow key is removably received within channels formed through a retainer and a rotatable obturator so that the lower end of the hollow key releasably engages the obturator. Selective rotation thereof allows eccentric spout formed in the obturator to align with an eccentric aperture formed in a valve plate. Fluids flow through the hollow key, the aligned spout and plate opening, the lower portion of the housing, and the opposing tubes for fluid transfer.

19 Claims, 6 Drawing Sheets

MAGNETICALLY SEALED INTRAVENOUS ACCESS VALVE

BACKGROUND OF THE INVENTION

1. Field of the Invention

The present invention relates to vascular access sets, and particularly to a magnetically sealed intravenous access valve permanently implanted for access to a patient's vein.

2. Description of the Related Art

Some medical procedures employ the infusion of therapeutic agents into living bodies over periods of time, thus making a syringe inconvenient or inappropriate. Such procedures have been used for the infusion of insulin, for example. In other cases, monitoring of internal body conditions with small sensors or other devices also makes syringes and similar devices inappropriate for continued access to subcutaneous tissue. To provide access in either circumstance, ports have been implanted in patients that provide support for a flexible cannula implanted in the body. Ports typically provide a housing that has a mounting side that is held by tape, dressings or direct adhesive against the body. A flexible cannula extends from the housing into the body.

Ports used for infusion may be employed in combination with a delivery tube extending to the housing of the port and in communication with the cannula as a complete infusion set. The delivery tube of such an infusion set is in communication with the flexible cannula through an infusion fluid chamber in the port to deliver therapeutic agents. Diagnostic agents such as biosensors may be delivered in a similar manner.

To place such ports or infusion sets including such ports, insertion sets have been used. An insertion set typically includes the port and a rigid sharp, such as a needle, which is placed through the flexible cannula for insertion into the body. The needle typically extends through a resilient barrier, such as a resealable resilient mass, through a chamber and then axially through the cannula. Once the cannula has been positioned in the body, the port is positioned and the needle can be withdrawn. The resealing of the mass as the needle is withdrawn prevents fluid from leaking from the port while remaining in position at the site. Once the port has been placed with the flexible cannula extending into the body, the agent or agents can be delivered.

A first type of insertion set includes an infusion set having the port and a delivery tube in communication with the cannula. The insertion set needle accesses the housing through a different path than the delivery tube. The seal is typically bypassed by the delivery tube in this instance. Alternatively, the insertion set may be used with a port rather than a complete infusion set. The delivery tube is placed after insertion of the port to complete an infusion set. The same path is used for the insertion needle as part of the insertion set as is used for communicating the tube of the infusion set with the cannula. In this latter case, the delivery tube is associated with a hub, which includes a member able to pierce a resealable resilient mass for communication between the delivery tube and the cannula once the insertion set has been disassembled through retraction of the needle. Such sets, however, can be extremely difficult to use, and the implantation procedure itself can be time consuming and difficult. Additionally, such sets often include parts which can easily become unsealed, and must be repaired or replaced over time.

Mechanisms typically referred to as "inserters" have been used to rapidly insert the needle and cannula into the body at the site. For the infusion of insulin in particular, diabetics self medicate. Consequently, they, a family member or other care provider places the port for infusion. This can be emotionally and physically difficult when repeated infusions are required over long periods of time. Inserters alleviate this burden somewhat by making the placement of the needle automatic and quick. Further, pressure by the inserter about the targeted site reduces the sensation of pain.

Inserters typically include a housing with a driver slidable in the housing. The driver includes a socket to receive the insertion set. A spring is operatively placed between the housing and the driver to advance rapidly an insertion set positioned in the socket. A latch then controls the advancement of the driver. Such inserters, however, can be relatively difficult for the patient to use, and do not provide any sort of additional control over the open access to the patient's vascular system.

Patients with certain chronic conditions, such as diabetes and chronic renal disease, require frequent access to the circulatory system, e.g., drawing blood for glucose monitoring, hemodialysis through an intravenous catheter, etc. The constant need to access the patient's veins with subsequent removal of the syringe, catheter, or other access port occurs with such frequency that it becomes necessary to change the access site frequently due to the condition of the vasculature and surrounding tissues. The frequent puncture wounds also become potential sites for infection.

Thus, a magnetically sealed intravenous access valve solving the aforementioned problems is desired.

SUMMARY OF THE INVENTION

The magnetically sealed intravenous access valve is an implantable port and valve for vascular access. The magnetically sealed intravenous access valve includes a housing having an upper portion and a lower portion. The lower portion defines an open interior region and has a pair of longitudinally opposed apertures formed therethrough. The upper portion has an open upper end, which is in fluid communication with the lower portion. A pair of hollow tubes are provided for interconnection and communication with the patient's blood vessel. Each tube has longitudinally opposed first and second ends. The first ends are slidably received within the pair of longitudinally opposed apertures formed through the lower portion of the housing.

A valve plate is mounted on a flange in the upper portion of the housing. The valve plate has an eccentric aperture formed therethrough. A rotatable obturator is disposed within the upper portion of the housing and is positioned against an upper surface of the valve plate. The obturator has a channel formed axially therethrough that terminates in an eccentric spout formed in the lower end of the obturator. In use, selective rotation of the obturator aligns the eccentric spout with the eccentric aperture formed through the valve plate to form a continuous fluid passage from the obturator channel into the lower portion of the housing. The valve plate and the obturator are preferably securely abutted against one another by magnetic attraction to lessen or eliminate the need for gaskets.

A retainer has an upper portion and a lower portion. The lower portion is hollow and is disposed within the open upper end of the upper portion of the housing. The obturator is disposed within the lower portion of the retainer to retain the obturator within the upper portion of the housing. The upper portion of the retainer extends upward from the upper portion of the housing and has a retainer channel formed therethrough. The retainer channel is aligned with and communicates with the obturator channel.

A hollow key is used to selectively open and close the valve and also to inject medication into the patient's blood vessel, or withdraw blood from the blood vessel. The hollow key has opposed open upper and lower ends, and is removably inserted into the retainer and obturator channels so that the lower end of the hollow key releasably engages the obturator. In use, selective rotation of the hollow key aligns the eccentric opening in the lower surface of the obturator with the eccentric aperture formed through the valve plate. The hollow key is adapted for receiving a dose of medication, so that the patient or caregiver may insert the hollow key through the retainer and obturator channels and then rotate the hollow key to align the eccentric opening in the obturator with the eccentric aperture in the valve plate to inject the medication through the aperture. The medication flows into the lower portion of the housing and through the pair of hollow tubes into the blood vessel of the patient.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
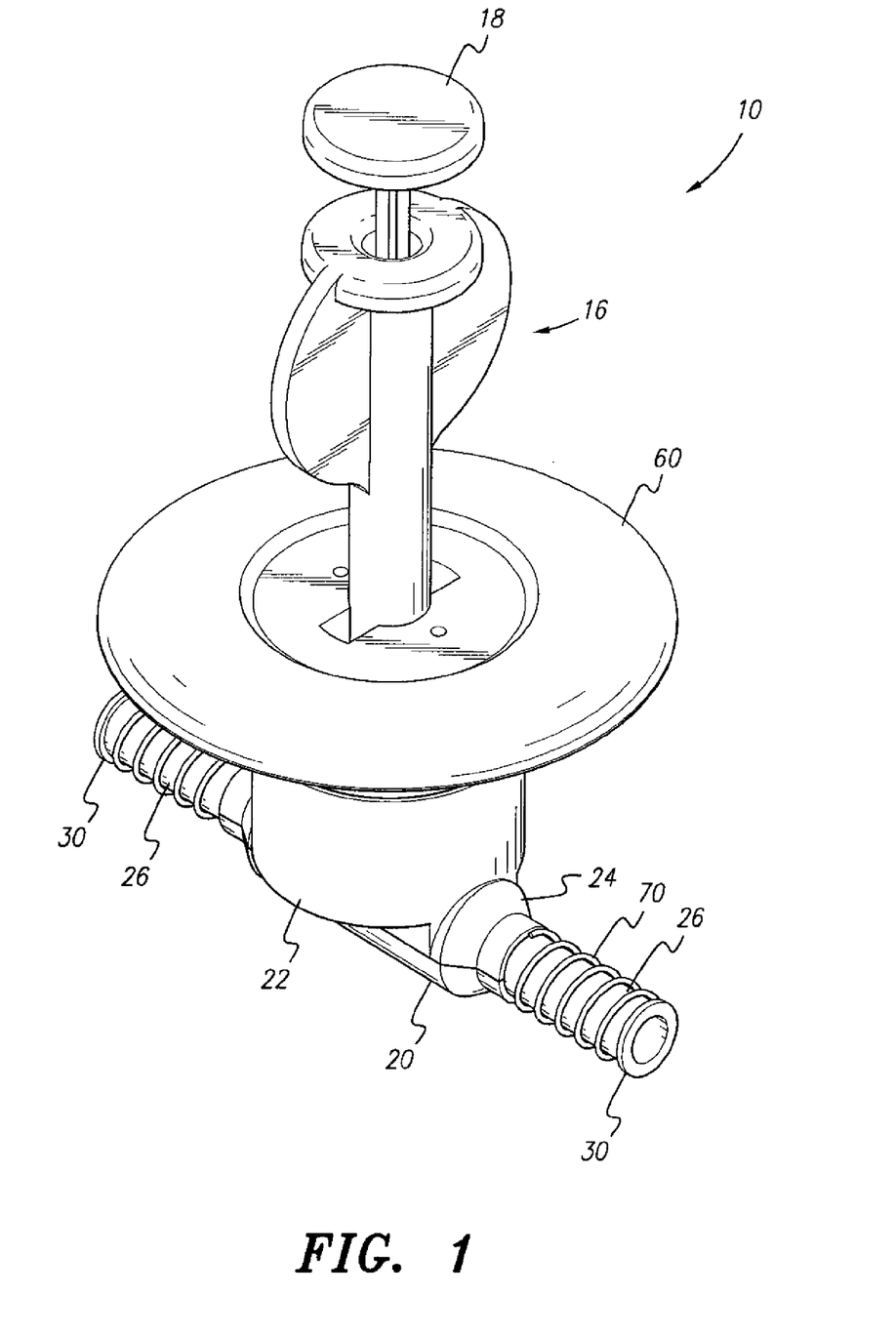
FIG. 1 is a perspective view of a magnetically sealed intravenous access valve according to the present invention, shown with the key inserted in the valve.
Figure 2:
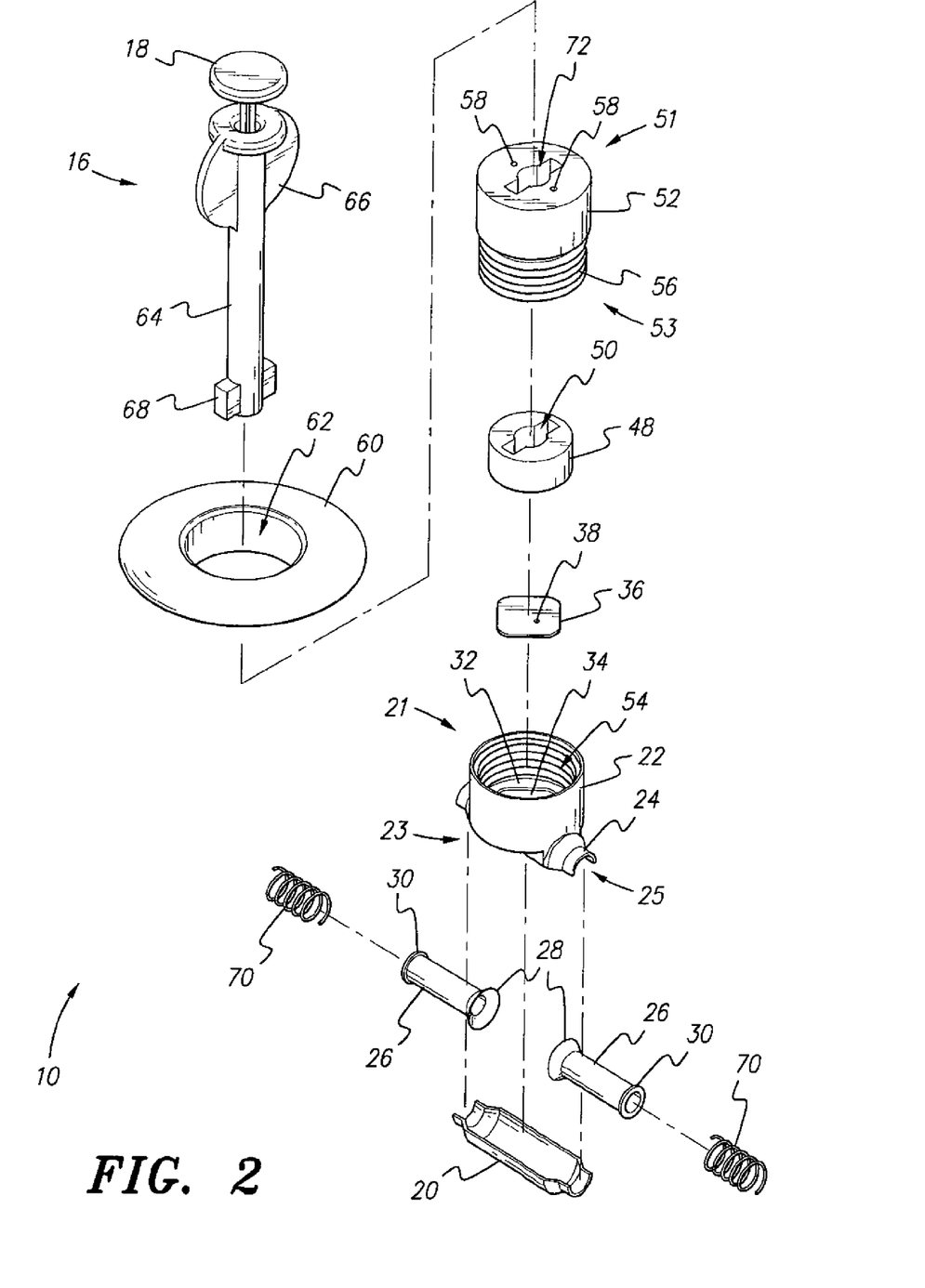
FIG. 2 is an exploded view of the magnetically sealed intravenous access valve according to the present invention.

The magnetically sealed intravenous access valve 10 is an implantable port and valve for vascular access, designed for permanent implantation in a patient's vein to permit withdrawal of blood samples and injection of medications without the need for repeated puncture wounds. As best seen in FIGS. 1 and 2, the magnetically sealed intravenous access valve 10 includes a housing 22 having an upper portion 21 and a lower portion defined by generally semicylindrical shells 23 and 20. The lower portion defines an open interior region 76 (shown in FIG. 4) and having a pair of longitudinally opposed apertures 25 formed therethrough. The lower semicylindrical shell 20 may be releasably attached to the upper semicylindrical shell 23 (e.g., a snap fit), or may be permanently attached by adhesive, welding, ultrasonic welding, or other metal or plastics manufacturing or joinery processes.

The upper portion 21 has an open upper end that is in fluid communication with the lower portion. A pair of hollow tubes 26 are provided for interconnection and communication with the patient's blood vessel. Each tube 26 has longitudinally opposed first and second ends 28, 30, respectively. The first ends 28 are slidably received within the pair of longitudinally opposed apertures 25 formed through the lower portion of the housing 22. During implantation, the hollow tubes 26 may be at least partially collapsed within the lower portion 23, but the hollow tubes 26 are fully extended when ready for interconnection with the patient's blood vessel. The lower portion of the housing 22 and the tubes 26 form a continuous passage for the flow of blood when the valve 10 is in the closed position.

Preferably, the lower portion of the housing 22 has a pair of longitudinally opposed frustoconical sections 24, the pair of longitudinally opposed apertures 25 being centrally and axially formed therethrough. Each first end 28 of each of the hollow tubes 26 is substantially frustoconical for mating with a respective one of the frustoconical sections 24 of the lower portion of the housing 22. It should be understood that the shape of the lower portion of the housing 22 and the mating first ends 28 may be varied. The pair of hollow tubes 26 are spring-biased against the lower portion 23 of the housing 22. Each second end 30 of each of the hollow tubes 26 preferably has a flange formed circumferentially therearound, and a helical spring 70 is mounted coaxially around the tube 26, the spring 70 bearing against the flange and the respective frustoconical section 24 of the lower portion of the housing 22, thereby biasing the tubes 26 to an extended position.

A valve plate 36 is mounted on an inwardly extending flange forming the floor 32 of the upper portion 21 of the housing 22. The valve plate 36 has an eccentric aperture 38 formed therethrough. The valve plate 36 the opening 34 formed by the flange. The valve plate 36 is being substantially diamond-shaped, but it should be understood that the valve plate 36 may have any desired shape. The valve plate 36 and the opening 34 preferably are not circular, which might cause rotation of the valve plate 36 in the housing 22, and the plate 36 may be fixed to the flange to further prevent rotation.

A rotatable obturator 48 is disposed within the upper portion 21 of the housing 22 and is positioned against an upper surface of the valve plate 36. Preferably, the rotating obturator 48 and the valve plate 36 are magnetically secured together, thus minimizing the possibility of leakage of the valve. The obturator 48 may be formed from a neodymium-based magnetic material, for example, and the valve plate 36 may be formed from a ferromagnetic material, such as stainless steel or the like.

Figure 4:
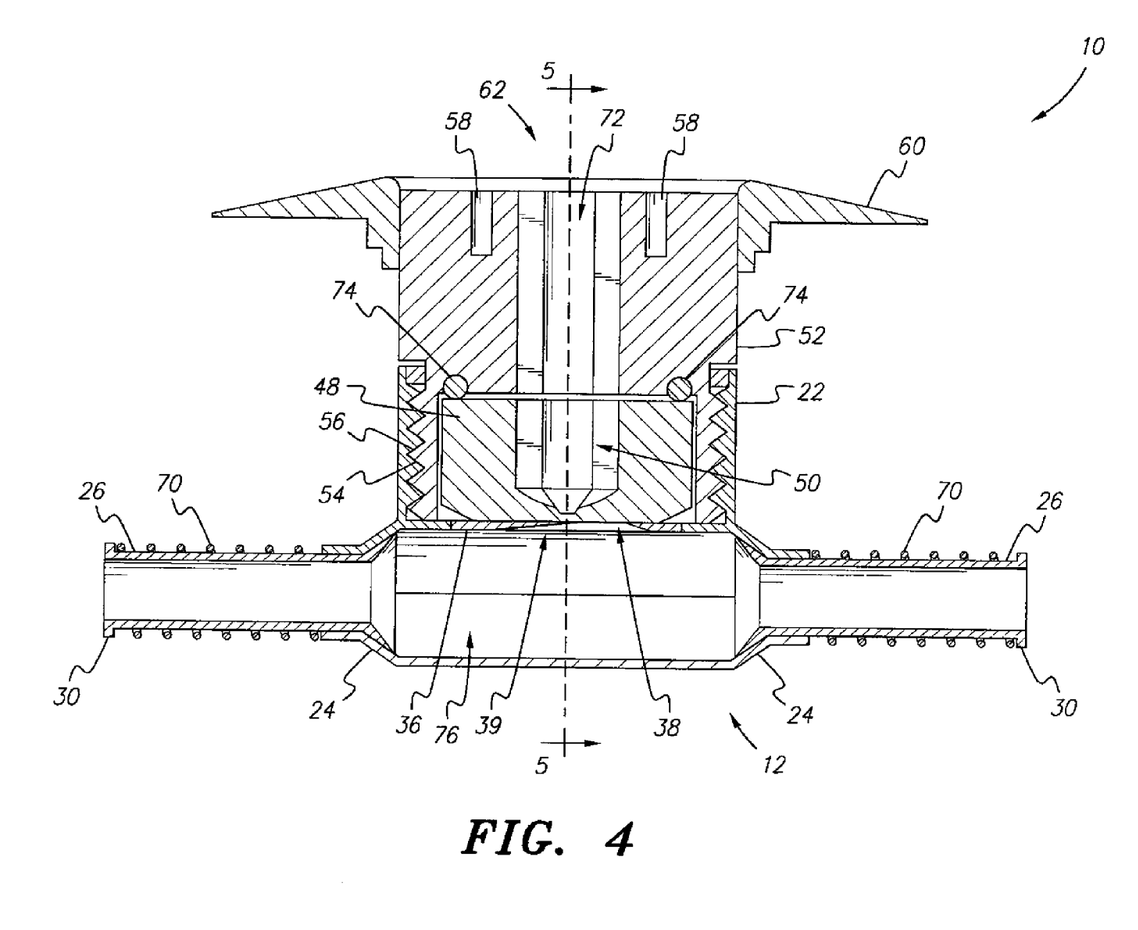
FIG. 4 is a front view in section of the magnetically sealed intravenous access valve according to the present invention.
Figure 5:
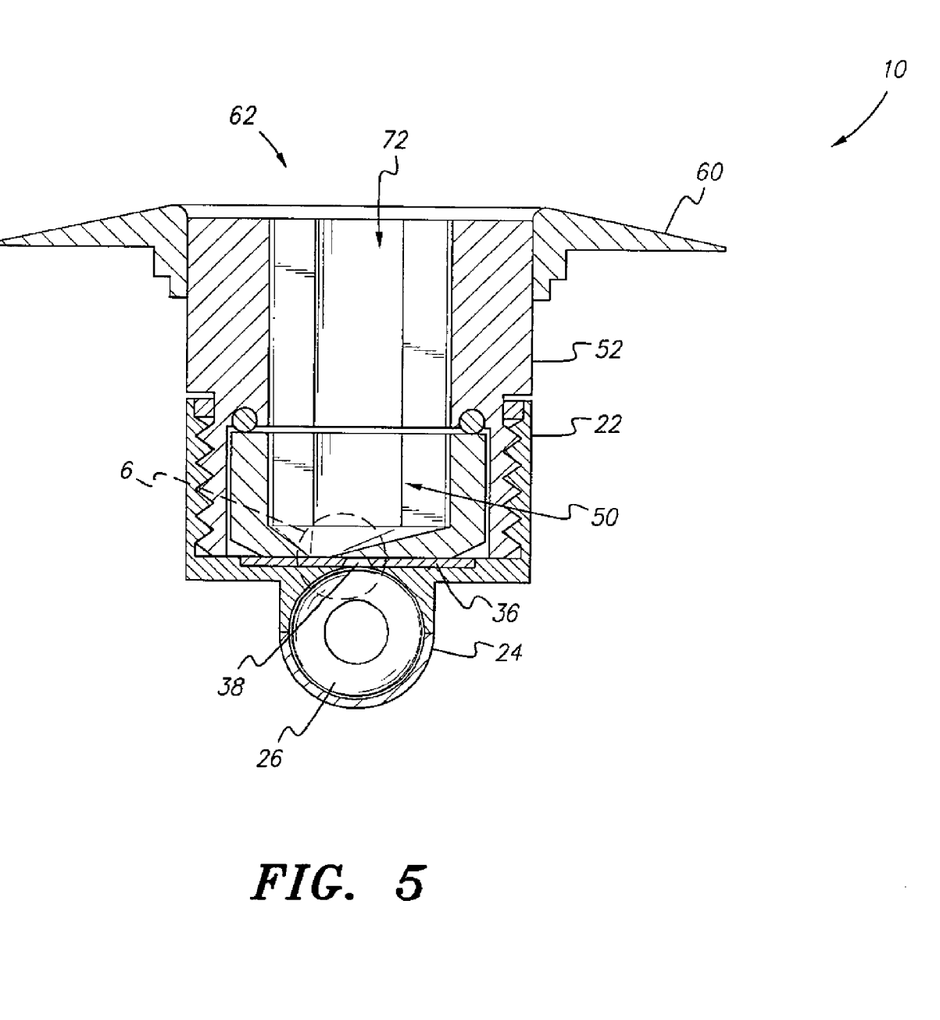
FIG. 5 is a sectional view taken along lines 5-5 of FIG. 4.
Figure 6:
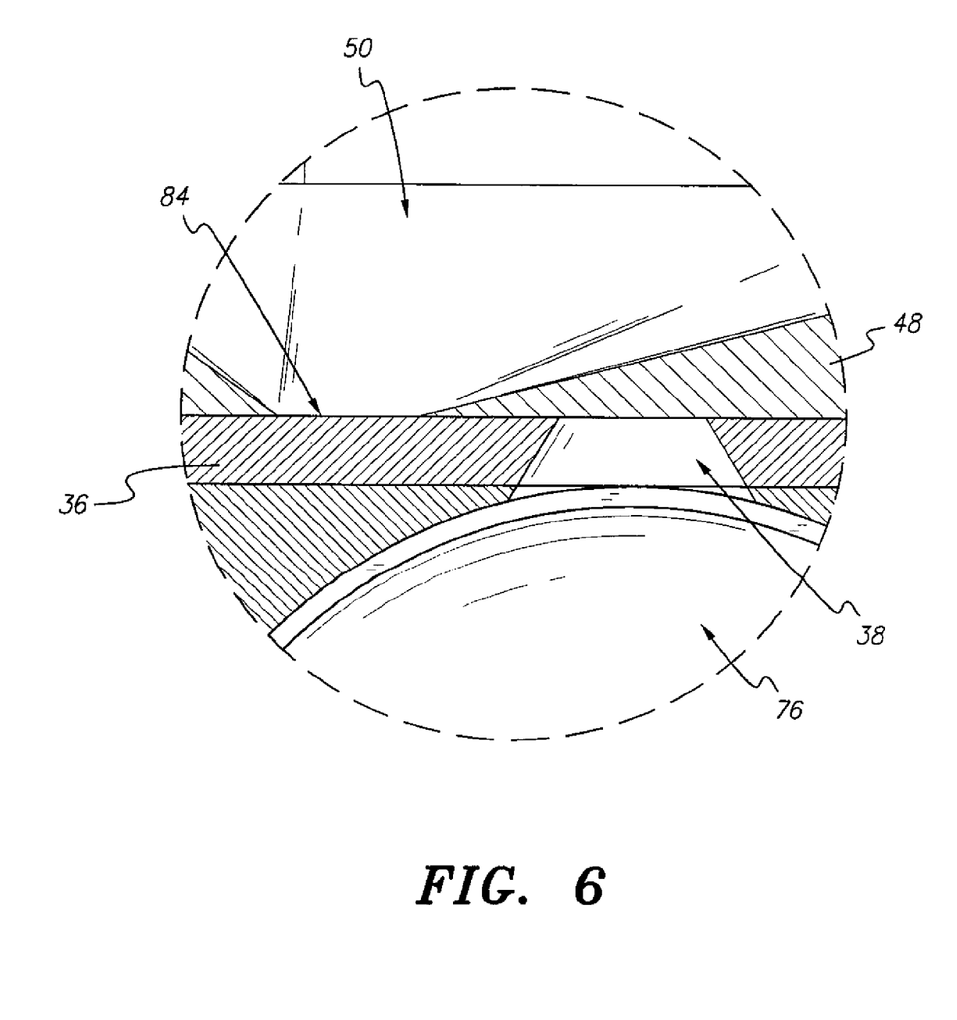
FIG. 6 is a detail view of area 6 in FIG. 5.

The obturator 48 has an obturator channel 50 formed axially therethrough. The channel 50 includes a central cylindrical bore and diametrically opposed keyways. Further, as best shown in FIGS. 5 and 6 (FIG. 6 is a detail view of area 6 of FIG. 5), the obturator channel 50 terminates in an eccentric spout 84 formed through a lower surface of the obturator 48. In use, selective rotation of the obturator 48 aligns the eccentric spout 84 with the eccentric aperture 38 formed through the valve plate 36 to form a continuous fluid passage from the obturator channel 50 into the lower portion 23 of the housing 22. As noted above, the valve plate 36 and the obturator 48 are preferably magnetically secured together to ensure a fluid-tight seal therebetween. As best shown in FIG. 4, a groove or slot 39 is formed in the lower surface of the valve plate 36 below the aperture 38. This groove or slot 39 is provided to prevent blood flowing through hollow tubes 26 and the open lower portion 23 from coagulating near or around aperture 38. Collection and coagulation of the blood can cause clots, which are dangerous to the patient and must be avoided.

A retainer 52 having an upper portion 51 and a hollow lower portion 53 is disposed in the open upper end of the upper portion 21 of the housing 22. The lower portion 53 of the retainer 52 is releasably secured to the upper portion 21 of the housing 22 through any suitable type of releasable engagement, such as through exemplary threads 54, 56. The obturator 48 is rotatable in the hollow lower portion 53 of the retainer 52, the retainer 53 securing the obturator 48 within the upper portion 21 of the housing 22. The upper portion 51 of the retainer 52 extending upwardly and outwardly from the upper portion 21 of the housing 22, as best shown in FIGS. 4 and 5. As shown in FIG. 4, ball bearings 74 or the like may be fitted within retainer 52 against an upper surface of obturator 48 to aid in the rotation thereof.

The retainer 52 has a retainer channel 72 formed therethrough. The retainer channel 72 is aligned with and communicates with the obturator channel 50. As shown, the retainer and obturator channels 72, 50, respectively, each preferably has a central cylindrical bore and diametrically opposed keyways. The channels are configured for removably receiving a hollow key 16.

The hollow key 16 is used to selectively open and close the valve, and also to inject medication into the patient's blood vessel or to withdraw blood samples. The hollow key 16 has opposed open upper and lower ends, and may be removably inserted through the retainer channel 72 and into the obturator channel 50 so that flanges or bits 68 at the lower end of the hollow key 16 slide through the keyways in the retainer channel releasably engage the keyways in the obturator channel 50. The hollow key 16 includes cylindrical tube 64 and a plunger 18 slidable in the tube 64. The bits 68 drive rotation of the obturator 48 when the hollow key 16 is rotated by the user. Additionally, a gripping member 66 may be mounted on an upper end of the hollow key tube 64.

Figure 3:
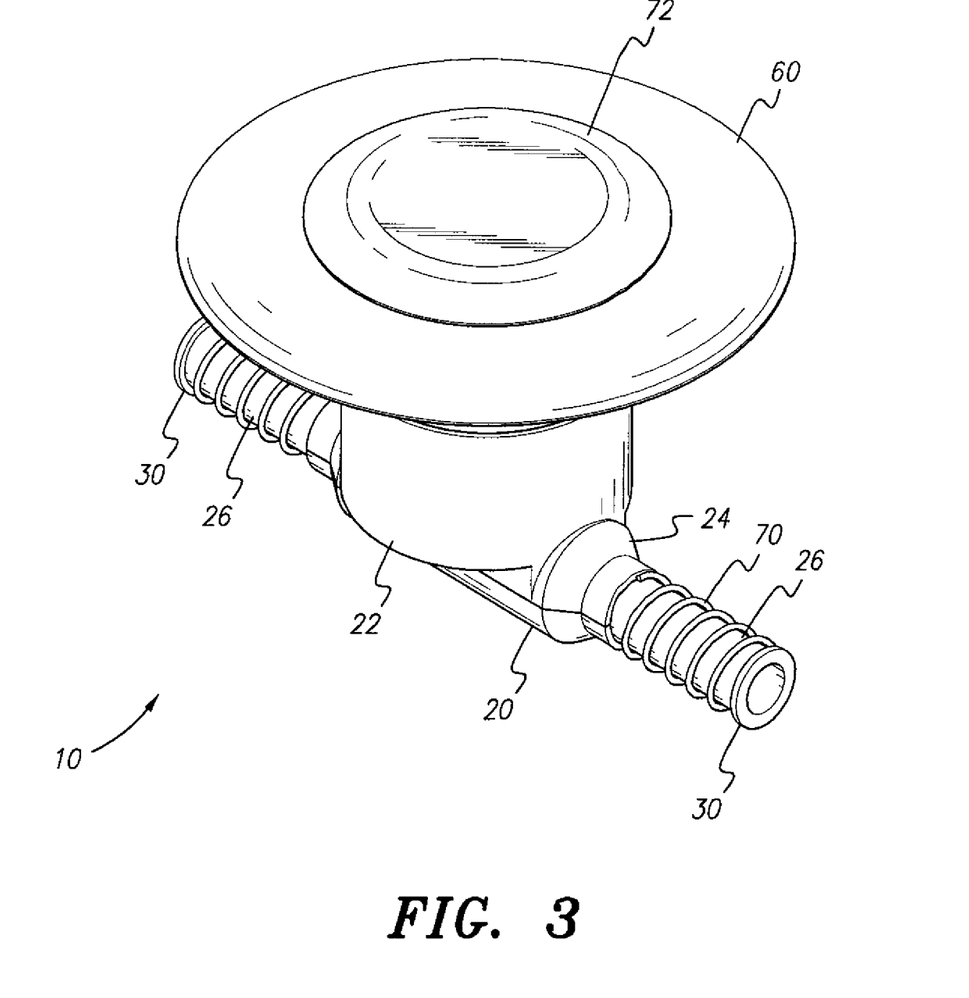
FIG. 3 is a perspective view of the magnetically sealed intravenous access valve of FIG. 1 with a sealing cap installed.

Further, an annular member 60 having a central opening 62 may be provided. The annular member 60 is preferably an annular graft formed from the patient's tissue, either through extraction or culturing. The tissue is formed into annulus 60 and is mounted on the retainer 52 (as best shown in FIGS. 1, 4 and 5), the upper surface of the retainer 52 extending into the central opening 62. When implanted in the patient, the annulus 60 is grafted into the skin of the patient, thus allowing the device 10 to be securely implanted with minimal risk of rejection, irritation or inflammation. Additionally, a cap 72, as shown in FIG. 3, may be provided for covering and sealing the central opening 62 formed through the annular graft 60 and the open upper end of the retainer channel 52. The cap 72 may include prongs or the like for removable frictional engagement with recesses 58 formed in an upper surface of the retainer 52.

In use, selective rotation of the hollow key 16 allows the eccentric spout 84 formed through the lower end of the obturator 48 to align with the eccentric aperture 38 formed through the valve plate 36. The hollow key 16 is adapted for receiving a dose of medication, such as insulin or the like, so that the patient or caregiver may insert the hollow key 16 through the retainer and obturator channels 72, 50, respectively, and then rotate the hollow key 16 to align the spout 84 formed in the obturator 48 with the aperture 38 formed through the valve plate 36 to inject the dosage of medication through the aperture 38. The medication flows through the open region 76 of the lower portion of the housing 22, where it mixes with the patient's blood and flows into the patient's vascular system via the pair of hollow tubes 26. Alternatively, the hollow tube 64 may be used as a cannula for the delivery of dialysis fluids for hemodialysis, or the key 16 may be used as a syringe for the removal of blood samples for glucose monitoring or the like. When the valve is in the open position, the lower end of hollow key 16 is received fully within the channel 50 of obturator 48, and the keyways of channel 50 are positioned substantially orthogonal to the keyways of retainer channel 72. Thus, when the obturator 48 is rotated to open the valve, the bits 68 of key 16 lock the key 16 in this position. Thus, the valve may only be opened when the key 16 is fully inserted and rotated, and the key 16 cannot be removed while the valve is in the open position. In order to remove the key 16, the obturator 48 must be rotated back into the closed position, such that the keyways of channel 50 align with the keyways of channel 72.

The magnetically sealed intravenous access valve 10 may be made from titanium, polytetrafluoroethylene (PTFE, or teflon), of other biocompatible material conventionally used for the manufacture of implants (although, as described above, the obturator 48 may be a neodymium magnet and the plate 36 may be stainless steel or other ferromagnetic material).

It is to be understood that the present invention is not limited to the embodiments described above, but encompasses any and all embodiments within the scope of the following claims.

I claim:

1. A magnetically sealed intravenous access valve, comprising:
    a housing having an upper portion and a lower portion, the lower portion defining an open interior region and having a pair of longitudinally opposed apertures formed therethrough, the upper portion having an open upper end in communication with the lower portion;
    a pair of hollow tubes, each of the tubes having longitudinally opposed first and second ends, the first ends being slidably disposed within the pair of longitudinally opposed apertures formed through the lower portion of the housing, the tubes being adapted for connecting the valve inline in a patient's vein, the lower portion of the housing and the tubes forming a continuous passage for the flow of blood;
    a valve plate mounted in the upper portion of the housing, the valve plate having an eccentric aperture formed therethrough;
    an obturator rotatable within the upper portion of the housing and positioned against an upper surface of the valve plate, the obturator having an upper and lower end and an obturator channel formed axially therein, the obturator channel terminating in an eccentric spout formed in the lower end of the obturator so that selective rotation of the obturator aligns the eccentric spout with the eccentric aperture formed through the valve plate to form a continuous passage from the obturator channel into the lower portion of the housing, the valve plate and the obturator being retained in abutting relation by magnetic attraction;
    a retainer having an upper portion and a hollow lower portion, the lower portion being disposed in the open upper end of the upper portion of the housing, the obturator being rotatably disposed within the lower portion of the retainer to secure the obturator within the upper portion of the housing, the upper portion of the retainer extending upwardly from the upper portion of the housing and having a retainer channel formed therethrough, the retainer channel being aligned with and communicating with the obturator channel; and
    a hollow key having opposed open upper and lower ends, the hollow key being removably received within the retainer and obturator channels so that the lower end of the hollow key releasably engages the obturator;
    wherein selective rotation of the hollow key aligns the eccentric spout formed in the lower end of the obturator with the eccentric aperture formed through the valve plate, the hollow key being adapted for transfer of fluid between the key and the lower portion of the housing.

2. The magnetically sealed intravenous access valve as recited in claim 1, wherein said valve plate is disposed on a flange within the upper portion of said housing.

3. The magnetically sealed intravenous access valve as recited in claim 2, further comprising a pair of springs, the springs being coaxially disposed around said tubes, the springs biasing said tubes to an extended position.

4. The magnetically sealed intravenous access valve as recited in claim 3, wherein the lower portion of said housing has a pair of longitudinally opposed frustoconical sections, the pair of longitudinally opposed apertures being centrally and axially formed therethrough.

5. The magnetically sealed intravenous access valve as recited in claim 4, wherein the first end of each said tube is substantially frustoconical for mating with a respective one of the frustoconical sections of the lower portion of said housing.

6. The magnetically sealed intravenous access valve as recited in claim 5, wherein the second end of each said hollow tube has a flange formed circumferentially therearound, the springs bearing against the flanges.

7. The magnetically sealed intravenous access valve as recited in claim 1, wherein the retainer and obturator channels each has a central cylindrical bore and diametrically opposed keyways extending therefrom.

8. The magnetically sealed intravenous access valve as recited in claim 7, wherein said key comprises:
an elongated, hollow, cylindrical key tube having an upper end and a lower end;
a plunger slidably disposed within the key tube; and
a pair of diametrically opposed bits at the lower end of the key tube, the tube being slidably insertable through the central bore and the bits being slidable through the keyways of the channels in the retainer and the obturator, the bits engaging the obturator when the key is turned to open and close the valve.

9. The magnetically sealed intravenous access valve as recited in claim 8, further comprising a gripping member mounted on an upper end of the hollow key tube.

10. The magnetically sealed intravenous access valve as recited in claim 1, further comprising an annular tissue graft having a central opening, the annular tissue graft being mounted on said retainer, said retainer having an upper surface flush with the plate.

11. The magnetically sealed intravenous access valve as recited in claim 1, wherein the lower portion of said retainer is externally threaded and the upper portion of said housing is internally threaded, said retainer being threaded into said housing.

12. An intravenous access valve, comprising:
a housing having an upper portion and a lower portion, the lower portion defining an open interior region and having a pair of longitudinally opposed apertures formed therethrough, the upper portion having an open upper end and being in communication with the lower portion;
a pair of hollow tubes having longitudinally opposed first and second ends, the first ends thereof being slidably disposed within the pair of longitudinally opposed apertures formed through the lower portion of the housing, each of the hollow tubes being spring-biased against the lower portion of the housing, the tubes being adapted for connecting the valve inline in a patient's vein, the lower portion of the housing and the tubes forming a continuous passage for the flow of blood;
a valve plate mounted in the upper portion of the housing, the valve plate having an eccentric aperture formed therethrough;
an obturator rotatable within the upper portion of the housing and positioned against an upper surface of the valve plate, the obturator having an upper and lower end and an obturator channel formed axially therein, the obturator channel terminating in an eccentric spout formed in the lower end of the obturator so that selective rotation of the obturator aligns the eccentric spout with the eccentric aperture formed through the valve plate to form a continuous passage from the obturator channel into the lower portion of the housing, the valve plate and the obturator being retained in abutting relation by magnetic attraction;
a retainer having an upper portion and a hollow lower portion, the lower portion being disposed in the open upper end of the upper portion of the housing, the obturator being rotatably disposed within the lower portion of the retainer to secure the obturator within the upper portion of the housing, the upper portion of the retainer extending upwardly from the upper portion of the housing and having a retainer channel formed therethrough, the retainer channel being aligned with and communicating with the obturator channel, the retainer having an upper surface;
a cap releasably covering the upper surface of the retainer;
a hollow key having opposed open upper and lower ends, the hollow key being removably received within the retainer and obturator channels so that the lower end of the hollow key releasably engages the obturator;
wherein selective rotation of the hollow key aligns the eccentric spout formed in the lower end of the obturator with the eccentric aperture formed through the valve plate, the hollow key being adapted for transfer of fluid between the key and the lower portion of the housing.

13. The intravenous access valve as recited in claim 12, wherein said obturator comprises a magnet and said valve plate is made from ferromagnetic material.

14. The intravenous access valve as recited in claim 12, wherein the lower portion of said housing has a pair of longitudinally opposed frustoconical sections, the pair of longitudinally opposed apertures being centrally and axially formed therethrough.

15. The intravenous access valve as recited in claim 12, wherein the first end of each said hollow tube is substantially frustoconical for mating with a respective one of the frustoconical sections of the lower portion of said housing.

16. The intravenous access valve as recited in claim 12, wherein each said second end of each said hollow tube has a flange formed circumferentially therearound.

17. The intravenous access valve as recited in claim 12, wherein said housing, said retainer, and said tubes are made from titanium.

18. The intravenous access valve as recited in claim 12, wherein said housing, said retainer, and said tubes are made from polytetrafluoroethylene.

19. The magnetically sealed intravenous access valve as recited in claim 12, wherein the retainer and obturator channels each have a central cylindrical bore and a diametrically opposed pair of keyways extending from the central bore, and wherein said hollow key comprises:
an elongated, hollow, cylindrical key tube having an upper end and a lower end;
a plunger slidably disposed within the key tube; and
a pair of diametrically opposed bits at the lower end of the key tube, the tube being slidably insertable through the central bore and the bits being slidable through the keyways of the channels in the retainer and the obturator, the bits engaging the obturator when the key is turned to open and close the valve.

* * * * *